United States Patent
Dicorleto et al.

(10) Patent No.: US 9,468,427 B2
(45) Date of Patent: Oct. 18, 2016

(54) NAVIGATED INSTRUMENT WITH A STABILIZER

(71) Applicant: Medtronic Navigation, Inc., Louisville, CO (US)

(72) Inventors: Matthew F. Dicorleto, Boulder, CO (US); Marco Capote, Boulder, CO (US)

(73) Assignee: Medtronic Navigation, Inc., Louisville, CO (US)

( * ) Notice: Subject to any disclaimer, the term of this patent is extended or adjusted under 35 U.S.C. 154(b) by 52 days.

(21) Appl. No.: 14/628,868

(22) Filed: Feb. 23, 2015

(65) Prior Publication Data
US 2015/0164493 A1   Jun. 18, 2015

Related U.S. Application Data

(62) Division of application No. 13/432,057, filed on Mar. 28, 2012, now Pat. No. 8,961,500.

(51) Int. Cl.
*A61B 17/16* (2006.01)
*A61B 17/00* (2006.01)

(52) U.S. Cl.
CPC ..... *A61B 17/00234* (2013.01); *A61B 17/1622* (2013.01); *A61B 34/20* (2016.02); *A61B 2017/00991* (2013.01); *A61B 2034/2055* (2016.02); *A61B 2090/035* (2016.02); *A61B 2090/0812* (2016.02); *A61B 2090/3983* (2016.02)

(58) Field of Classification Search
CPC .......... A61B 1/00; A61B 17/00; A61B 5/00; A61B 5/05; A61F 4/00; A61F 5/04; B65G 11/00
USPC .................. 600/424, 210, 301, 229; 606/59; 119/843
See application file for complete search history.

(56) References Cited

U.S. PATENT DOCUMENTS

| | | | |
|---|---|---|---|
| 6,021,343 A | 2/2000 | Foley et al. | |
| 7,931,650 B2 | 4/2011 | Winquist et al. | |
| 8,961,500 B2 | 2/2015 | Dicorleto et al. | |
| 2004/0054489 A1 | 3/2004 | Moctezuma De La Barrera et al. | |
| 2004/0171930 A1 | 9/2004 | Grimm et al. | |

(Continued)

OTHER PUBLICATIONS

International Preliminary Report on Patentability and Written Opinion mailed Oct. 9, 2014 for PCT/US2013/033479 claiming benefit of U.S. Appl. No. 13/432,057, filed Mar. 28, 2012.

(Continued)

*Primary Examiner* — William Thomson
*Assistant Examiner* — Victor Shapiro
(74) *Attorney, Agent, or Firm* — Harness, Dickey (57) ABSTRACT

A stabilizer for use with a trackable surgical instrument can include a first member, a second member and a retaining member. The first member can have a first annular body portion and a first pair of legs extending therefrom. The first annular body portion can include a plurality of locating slots for engaging a selectively positionable portion of a surgical instrument. The second member can have a second annular body portion and a second pair of legs extending therefrom. The second annular body can engage a drive device of the surgical instrument. The first pair of legs can be telescopically coupled with and adjustable relative to the second pair of legs such that the first member can be axially adjustable relative to the second member. The retaining member can cooperate with at least one leg to retain the first member adjustably coupled to the second member.

20 Claims, 6 Drawing Sheets

(56) References Cited

U.S. PATENT DOCUMENTS

| | | |
|---|---|---|
| 2004/0230200 A1 | 11/2004 | Peterson |
| 2006/0015018 A1 | 1/2006 | Jutras et al. |
| 2007/0270685 A1 | 11/2007 | Kang et al. |
| 2009/0101084 A1 | 4/2009 | Robinson et al. |
| 2009/0118742 A1 | 5/2009 | Hartmann et al. |
| 2010/0081886 A1 | 4/2010 | Komuro |
| 2010/0210916 A1 | 8/2010 | Hu et al. |
| 2011/0263971 A1 | 10/2011 | Nikou et al. |
| 2013/0261609 A1 | 10/2013 | Dicorleto et al. |

OTHER PUBLICATIONS

International Search Report and Written Opinion for PCT/US2013/033479 mailed Jul. 12, 2013, claiming benefit of U.S. Appl. No. 13/432,057, filed Mar. 28, 2012.

NAVIGATED INSTRUMENT WITH A STABILIZER

CROSS-REFERENCE TO RELATED APPLICATIONS

This application is a divisional of patent application Ser. No. 13/432,057 filed Mar. 28, 2012. The entire disclosure of the above application is incorporated herein by reference.

FIELD

The present disclosure relates generally to navigated instruments and, more particularly, to a navigated instrument having a stabilizer.

BACKGROUND

This section provides background information related to the present disclosure which is not necessarily prior art.

Computer assisted image guided medical and surgical navigation systems are known and used to generate images in order to assist a doctor during a surgical procedure. In general, these image guided systems use images of a body part, such as CT scans, taken before surgery to generate images on a display, such as a monitor screen. These images are used during surgery for illustrating the position of a surgical instrument with respect to the body part. The systems typically include tracking devices such as, for example, a light emitting diode array mounted on a surgical instrument as well as a body part, a digitizer to track in real time the position of the body part and the instrument used during surgery, and a monitor screen to display images representing the body and the position of the instrument relative to the body part as the surgical procedure is performed.

While such known surgical instruments have worked for their intended purpose, there remains a need in the art for a surgically navigable instrument for use with these image guided systems that is simple to use and manipulate.

SUMMARY

This section provides a general summary of the disclosure, and is not a comprehensive disclosure of its full scope or all of its features.

In one form, a stabilizer for use with a trackable surgical instrument is provided in accordance with various aspects of the present teachings. The stabilizer can include a first member, a second member and a retaining member. The first member can have a first annular body portion at a distal end thereof and a first pair of legs extending therefrom and defining a proximal end of the first member. The first annular body portion can include a plurality of locating slots that can be adapted to engage a selectively positionable portion of the surgical instrument. The second member can have a second annular body portion at a proximal end thereof and a second pair of legs extending therefrom and defining a distal end of the second member. The second annular body can be adapted to engage a drive device of the surgical instrument. The first pair of legs can be telescopically coupled with and adjustable relative to the second pair of legs such that the first member can be axially adjustable relative to the second member. The retaining member can be configured to cooperate with at least one leg of the first and second pair of legs to retain the first member adjustably coupled to the second member.

In another form, a trackable surgical instrument is provided in accordance with various aspects of the present teachings. The surgical instrument can include a drive device, a guide member, an instrument tip and a stabilizer. The guide member can have a tracking array coupled thereto. The instrument tip can be configured to be driven by the drive device and rotatable relative to the guide member. The stabilizer can include a first member and a second member. The first member can have a first body portion at a distal end and a first pair of legs extending therefrom and defining a proximal end of the first member. The first body portion can include a plurality of locating slots configured to selectively engage the guide member to position the guide member and the array in one of a plurality of rotational orientations relative to the drive device. The second member can have a second body portion at a proximal end thereof and a second pair of legs extending therefrom that define a distal end of the second member. The second body portion can be configured to engage the drive device. The first pair of legs can be telescopically coupled with and adjustable relative to the second pair of legs such that the first member can be axially adjustable relative to the second member.

In yet another form, a method of using a trackable surgical instrument is provided in accordance with various aspects of the present teachings. The method can include coupling a guide member to a drive device of the surgical instrument, where the guide member can be selectively rotatable relative to the drive device. The guide member can be rotatably adjusted relative to the drive device to position a tracking array coupled to the guide member in a selective rotational orientation relative to the drive device. The guide member can be selectively retained in the selective rotational orientation. A real-time position of the surgical instrument can be tracked via a tracking system in conjunction with the tracking array. The surgical instrument can be guided along a desired trajectory using at least position data generated by the tracking system.

Further areas of applicability will become apparent from the description provided herein. The description and specific examples in this summary are intended for purposes of illustration only and are not intended to limit the scope of the present disclosure.

DRAWINGS

The present teachings will become more fully understood from the detailed description, the appended claims and the following drawings. The drawings are for illustrative purposes only of selected embodiments and not all possible limitations, and are not intended to limit the scope of the present disclosure.

DETAILED DESCRIPTION

The following description is merely exemplary in nature and is not intended to limit the present disclosure, its application, or uses. It should be understood that throughout the drawings, corresponding reference numerals indicate like or corresponding parts and features. Exemplary embodiments are provided so that this disclosure will be thorough, and will fully convey the scope to those who are skilled in the art. Numerous specific details are set forth, such as examples of specific components, devices, systems and/or methods, to provide a thorough understanding of exemplary embodiments of the present disclosure. It will be apparent to those skilled in the art that specific details need not be employed, that exemplary embodiments may be embodied in many different forms and that neither should be construed to limit the scope of the disclosure. In some exemplary embodiments, well-known processes, well-known device structures, and well-known technologies are not described in detail.

Figure 1:
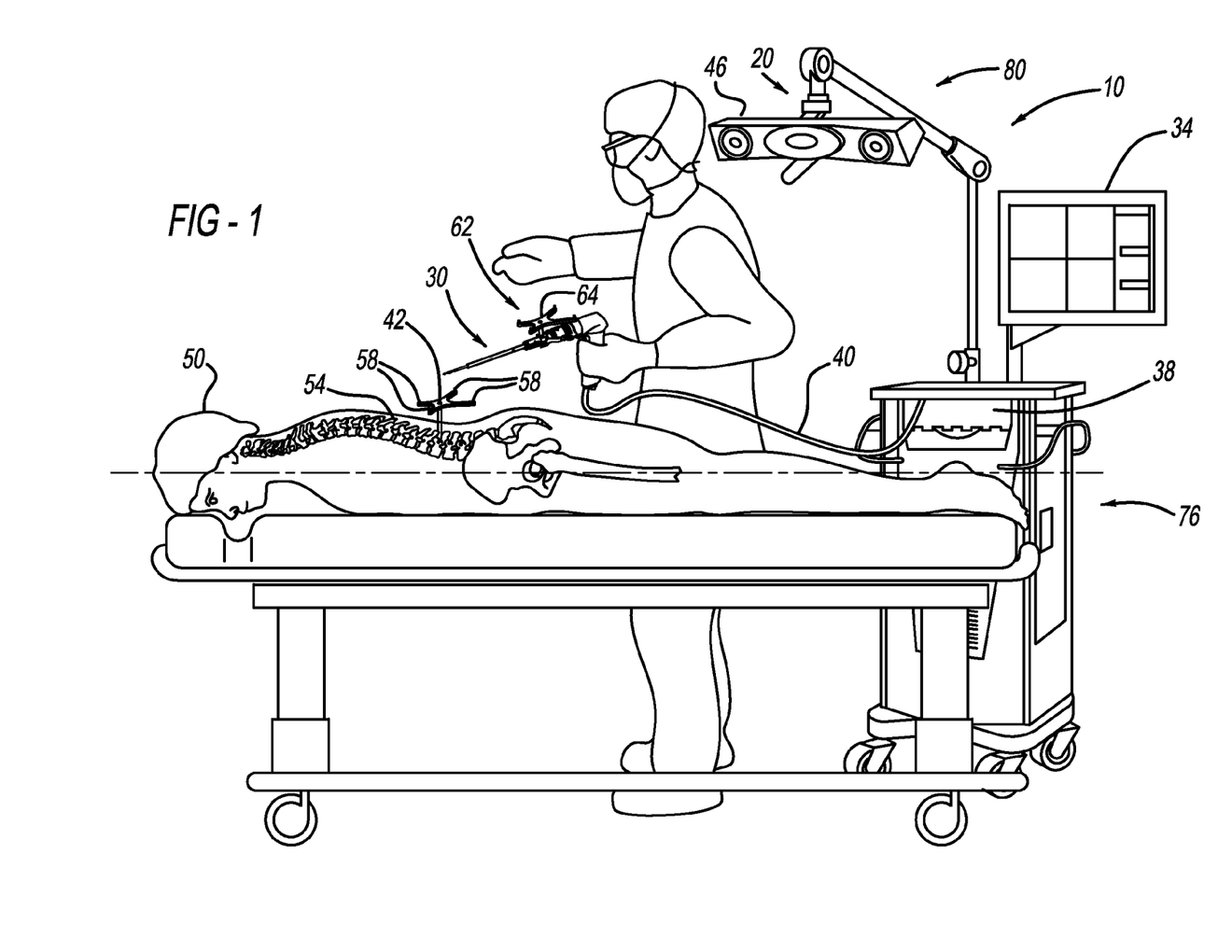
FIG. 1 is a diagram of an exemplary navigation system including an exemplary navigated surgical instrument in accordance with the teachings of the present disclosure.

Turning now to the drawings, FIG. 1 is a diagram illustrating an overview of a navigation system 10 that can be used for various procedures. The navigation system 10 can be used to track the position and orientation of various instruments. It should further be noted that the navigation system 10 may be used to navigate any type of instrument, implant, or delivery system, including: guide wires, arthroscopic systems, orthopedic implants, spinal implants, deep-brain stimulator (DBS) probes, etc. Moreover, these instruments may be used to navigate or map any region of the body. The navigation system 10 and the various instruments may be used in any appropriate procedure, such as one that is generally minimally invasive, arthroscopic, percutaneous, stereotactic, or an open procedure.

With continuing reference to FIG. 1, the navigation system 10 can include an optical tracking system 20 for use in tracking an exemplary surgical instrument 30. Exemplary optical tracking systems can include the StealthStation® Treon® and the StealthStation® Tria® both sold by Medtronic Navigation, Inc. The navigation system 10 can be used to generate and display a real time position of a body part and the position of instrument 30 relative to the body part. An image can be generated on monitor 34 from an image data set stored in a controller, such as computer 38, usually generated preoperatively by any scanning technique such as by a CAT scanner, magnetic resonance imaging, or C-arm fluoroscopic imaging. The image data set and the image generated can have reference or fiducial points for at least one body part for use in registration of image space to patient space. The reference points for the particularly body part can have a fixed spatial relation to the particular body part.

System 10 can also generally include a processor associated with computer 38 for processing image data. The computer 38 can be connected to monitor 34 and to instrument 30, such as line 40. The computer 38, in conjunction with a reference frame array or dynamic reference frame (DRF) 42 and a sensor array or optical detector 46 or other known position sensing unit, can track the real time position of the body part, such as a cranium 50 or a portion of a spinal column 54 associated with reference frame 42, and the instrument 30. Reference frame 42 can have optical reflectors or emitters 58 or other tracking devices providing tracking signals representing the position of the various body reference points. The tracking devices 58 can be either passive or active, as is known in the art. As will be discussed in greater detail below, instrument 30 can have a tracking device 62 shown as tracking array 64 that can provide tracking signals representing the position of the instrument during the procedure. The tracking array 64 can include emitters 68 (FIG. 2) that can be either passive (e.g., reflectors) or active (e.g., light emitting diodes).

The navigation system 10 can include a portable station 76 housing the monitor 34 and computer 38, as well as supporting the detector 46. Detector 46 can be adjustably mounted to station 76 with an adjustable arm assembly 80 such that detector 46 can be adjusted in various positions relative to station 76 and the subject body part. The detector 46 can receive signals from the emitters 58 and 68 of respective arrays 42 and 64. As discussed above, the signals can be generated by active emitters, such as light emitting diodes, or can be reflections from passive emitters, such as reflectors, where the arrays 42 and 64 are in the field of view of detector 46. In either case, the detector can receive and triangulate the signals generated by emitters 58 and tracking array 64 in order to identify during the procedure the relative position of each of the reference points and the instrument. Computer 38 can then superimpose an icon representing the instrument 30 on the image data set according to the identified relative position of each of the reference points during the procedure. Computer 38 can also generate an image data set representing the position of the body elements and the instrument 30 during the procedure.

The structure and operation of an optical image guided surgery system is well known in the art and need not be discussed further here. Nevertheless, a further discussion of optical tracking systems, along with other tracking systems that can be used with instrument 30, such as an electromagnetic tracking system, can be found in U.S. Pat. No. 6,021,343 and U.S. Pub. No. 2009/0118742 assigned to Medtronic Navigation, Inc., the disclosures of which are hereby incorporated by reference in their entirety.

Turning now to FIGS. 2-6, instrument 30 will now be discussed in greater detail in accordance with the principles of the present disclosure. Instrument 30 can include a guide member 100, an interchangeable instrument tip 104, an interchangeable driving device 108 and a stabilizer 110. The tracking array 64 can be affixed to guide member 100 in either a removable or permanent fashion. The instrument tip 104 can include a proximal end 112 having a male connector 116 and a distal end 120 having a female connector configured to receive a cutting device or other tool, such as a drill bit 124. It should be appreciated that the tool could be any of a variety of instruments used in surgery such as taps, awls, and shaped tools for interacting with a work piece. It should also be appreciated that while instrument tip 104 is shown with a configuration to receive a separate drill bit 124, the drill bit 124 could also be integral with instrument tip 104.

The proximal end 112 of instrument tip 104 can be positioned though a passage 132 (FIG. 4) in guide member 100 such that instrument tip 104 extends through the guide member 100. Instrument tip 104 can include a bushing 136 having an attachment arrangement 144 configured to removably rotatably couple instrument tip 104 to guide member 100. In one exemplary configuration, bushing 136 can include an annular groove 138 configured to engage a coupling arrangement 148 (FIG. 4) associated with guide member 100. Bushing 136, when rotatably engaged with guide member 100, can engage a distal end 152 of guide member 100. To remove instrument tip 104 from guide member 100, a lever 158 (FIG. 4) of coupling arrangement 148 can be pivoted to release bushing 136, and thus instrument tip 104 from guide member 100. It should be appreciated that while the instrument tip 104 is shown as an integral structure extending through the guide member 100, instrument tip 104 could alternatively engage a drive shaft associated with guide member 100, as set forth in U.S. Pat. No. 6,021,343, which is incorporated by reference herein in its entirely.

Guide member 100 can include distal end 152, a proximal end 162 and the tracking array 64 discussed above. Tracking array 64 and guide member 100, if not constrained, can rotate with or relative to instrument tip 104. Thus, a surgeon or the like operating instrument 30 without the stabilizer 110, which will be discussed below in greater detail, could be required to hold the driving device 108 in one hand and the tracking array 64 in the other hand to fix or maintain a desired angular orientation of tracking array 64 in a field of view of detector 46. Tracking array 64 can be coupled to guide member 100 with a post or shaft 166 positioning array 64 in spaced relation to guide member 100, as shown for example in FIGS. 2 and 3. The guide member 100 can be rotatable relative to instrument tip 104 so as to position the tracking array 64 within the field of view of the detector 46.

Driving device 108 can include a powered driving device, such as drill 170, or any other suitable driving means, such as an interchangeable drive handle, for rotationally driving instrument tip 104 via a drive member (not specifically shown). In this regard, driving device 108 can be any number of existing or specially designed handles and could be ratcheting, nonratcheting or motorized. Driving device 108 can include a female socket 174 (FIG. 3) associated with the drive member and configured to removably receive male connector 116.

The stabilizer 110 can be used to provide a fixed angular orientation of the tracking array 64 relative to the instrument 30 so as to not require the surgeon to hold the tracking array 64 while operating instrument 30. This can provide for, among other things, freeing up one of the surgeon's hands while using instrument 30 in an associated procedure. With stabilizer 110, array 64 can be positioned in various angular orientations relative to instrument 30 and a position of detector 46 to provide more flexibility for the surgeon during the procedure. For example, tracking array 64 can be positioned in an angular orientation for a left-handed surgeon and in an opposite angular orientation for a right-handed surgeon so as to not require moving detector 46 and or an operating table supporting the patient to have tracking array 64 within the field of view of detector 46.

Figure 2:
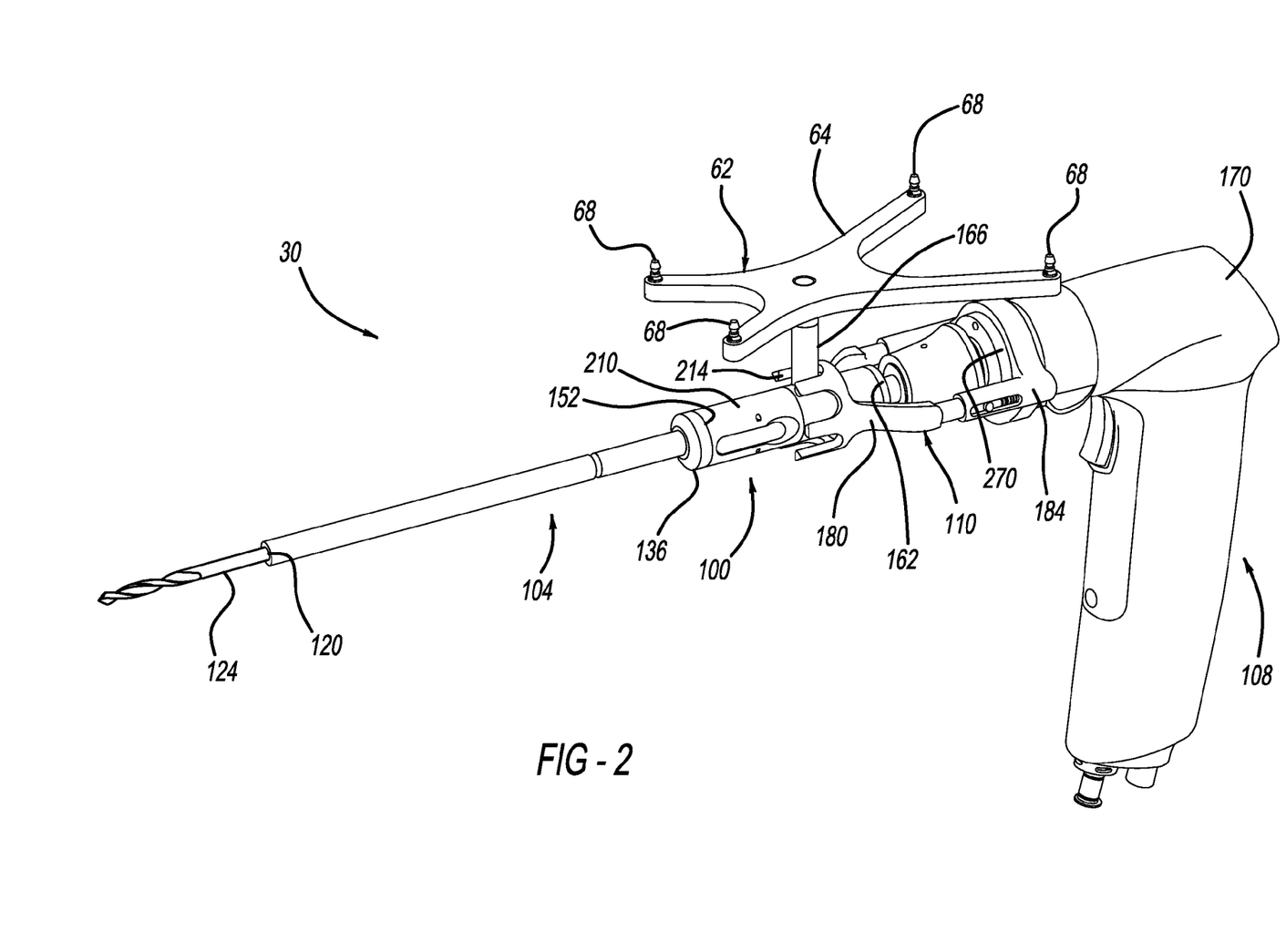
FIG. 2 is a perspective view of the exemplary instrument having a stabilizer in accordance with the teachings of the present disclosure.
Figure 5:
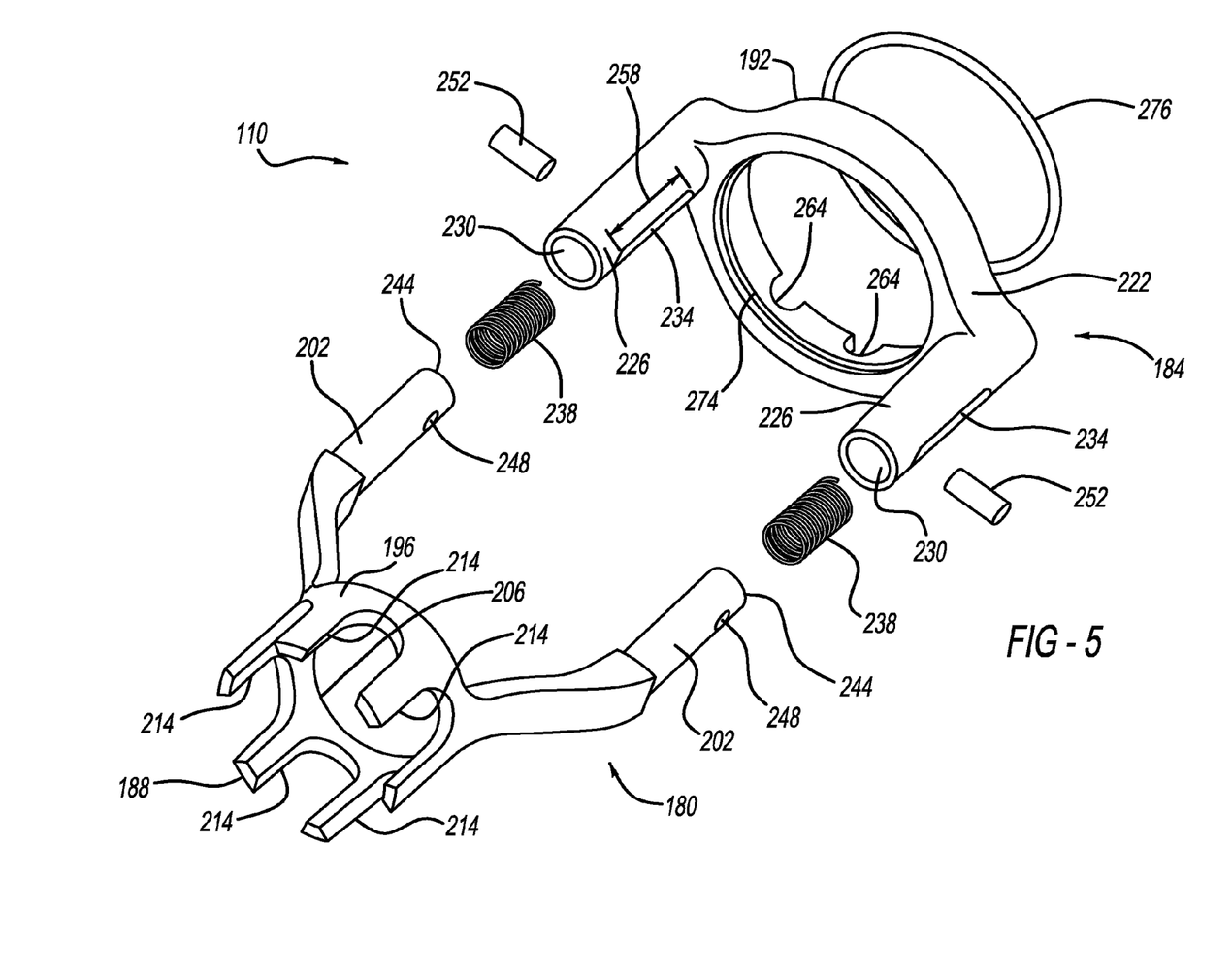
FIG. 5 is a perspective exploded view of the stabilizer in accordance with the teachings of the present disclosure.
Figure 6:
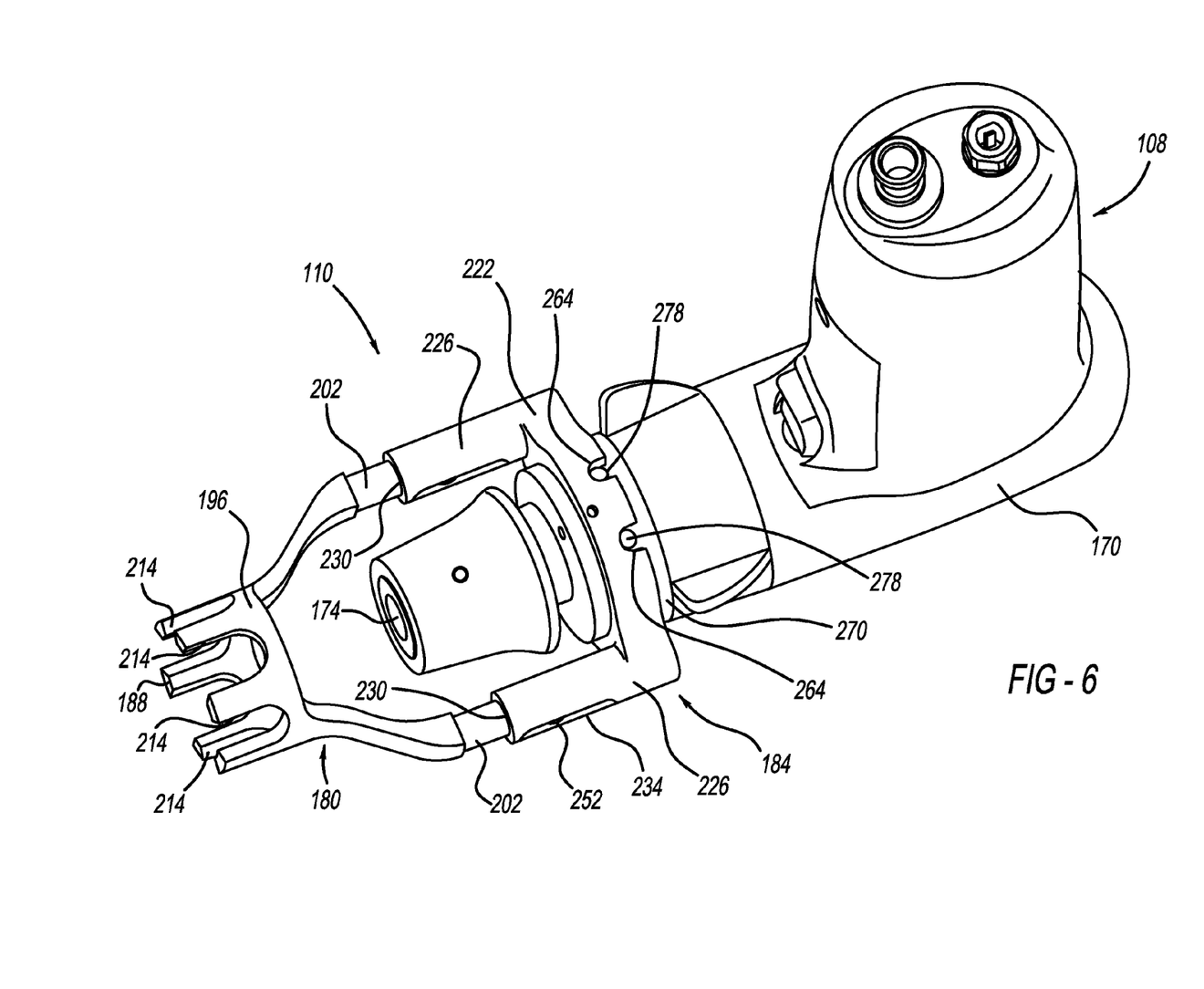
FIG. 6 is a bottom perspective view of the stabilizer engaged with an exemplary driving device in accordance with the teachings of the present disclosure.

With particular reference to FIGS. 2, 5 and 6, the stabilizer 110 will now be discussed in greater detail. The stabilizer 110 can include a first member 180 and a second member 184. First member 180 can define a distal end 188 of stabilizer 110 configured to removably engage guide member 100 and second member 184 can define a proximal end 192 configured to engage driving device 108. First member 180 can include an annular member 196 having first and second arms 202 extending axially therefrom. The annular member 196 can include an inner diameter 206 corresponding to an outer diameter 210 (FIG. 2) of guide member 100 such that annular member 196 can be slidably supported on guide member 100. Annular member 196 can include a plurality of depressions or cut-outs or locating slots 214 that define distal end 188 of stabilizer 110. As will be discussed in greater detail below, the plurality of locating slots 214 can be sized and shaped to selectively receive post 166 to position tracking array 64 in one of various desired angular orientations relative to driving device 108. It should be appreciated that the guide member 100 could alternatively include a plurality of cutouts and the annular member 196 could alternatively include a plurality of projections.

Second member 184 can include an annular member 222 that defines the proximal end 192 of stabilizer 110 and can include third and fourth arms 226 extending axially therefrom. The third and fourth arms 226 can include an internal bore 230 sized and shaped to telescopically receive the first and second arms 202 therein, as shown for example in FIG. 5. The third and fourth arms 226 can also include axially extending slots 234 extending through opposed sides of each of the third and fourth arms 226 so as to be in communication with the internal bores 230. A spring 238 can be received in each bore 230 and the first and second arms 202 can then be telescopically inserted into the bores 230 such that a distal end 244 of the arms 202 engages springs 238, as generally shown in FIG. 2 with reference to FIG. 5. It should be appreciated that the third and fourth arms 226 could alternatively be telescopically received in internal bores of the first and second arms 202.

The first and second arms 202 can include a transverse bore 248 proximate the distal end 244 configured to receive a retaining member, such as a pin 252. Pins 252 can be positioned in transverse bores 248 after the first and second arms 202 are inserted into the bores 230 of third and fourth arms 226, as generally shown in FIG. 5 with reference to FIG. 2. Pins 252 can retain the first member 180 in engagement with the second member 184 under the influence of springs 238 via engagement with first and second arms 202 and axially extending slots 234.

First member 180 can be axially adjusted relative to second member 184 by urging the first and second arms 202 axially toward and away from the proximal end 192 of stabilizer 110. Such action can telescopically move the first and second arms 202 further into and out of bores 230 relative to the third and fourth arms 226 and against the biasing force of springs 238. An axial length 258 of slots 234 can define an amount of adjustment of the first member 180 relative to the second member 184.

The annular member 222 of second member 184 can be configured to be received over a non-rotating or stationary housing portion 270 (FIG. 2) of driving device 108. The annular member 184 can include a pair of cut-outs or depressions 264 and an annular internal groove 274, as shown in FIG. 5. In one exemplary configuration, the internal groove 274 can be configured to receive an o-ring 276 or similar member to aid in retaining second member 184 in engagement with housing portion 270, as generally shown in FIG. 5 with reference to FIG. 2. It should be appreciated, however, that various other removable connection arrangements can be utilized to removably couple the second member 184 to housing portion 270 or another portion of driving device 108. The depressions 264 can be configured to receive a corresponding pair of projections 278 extending from housing portion 270 so as to fix the orientation of stabilizer 110 to the driving device 108, as generally shown in FIGS. 5 and 6.

In operation, torque applied by driving device 108 can be transmitted to instrument tip 104 via the connection of male connector 116 and female socket 174. Because instrument tip 104 is fixed axially in relation to guide member 100 via bushing 136, guide member 100 can remain axially stationary so as to not translate along instrument tip 104 during operation of instrument 30. The axial relationship between array 64 and instrument tip 104 can, therefore, remain constant. As a result, the relationship between array 64 and instrument tip 104 can also remain constant. Because the relationship between array 64 and instrument tip 104 is constant, the signals emitted by emitters 68 can be used by the computer assisted image guided surgical navigation system 10 to inform the surgeon of the position of instrument 30, indicating both the trajectory or orientation in three dimensional space of instrument 30 and a length of travel along the trajectory, i.e., the depth instrument tip 104 has been inserted into a body part.

Figure 3:
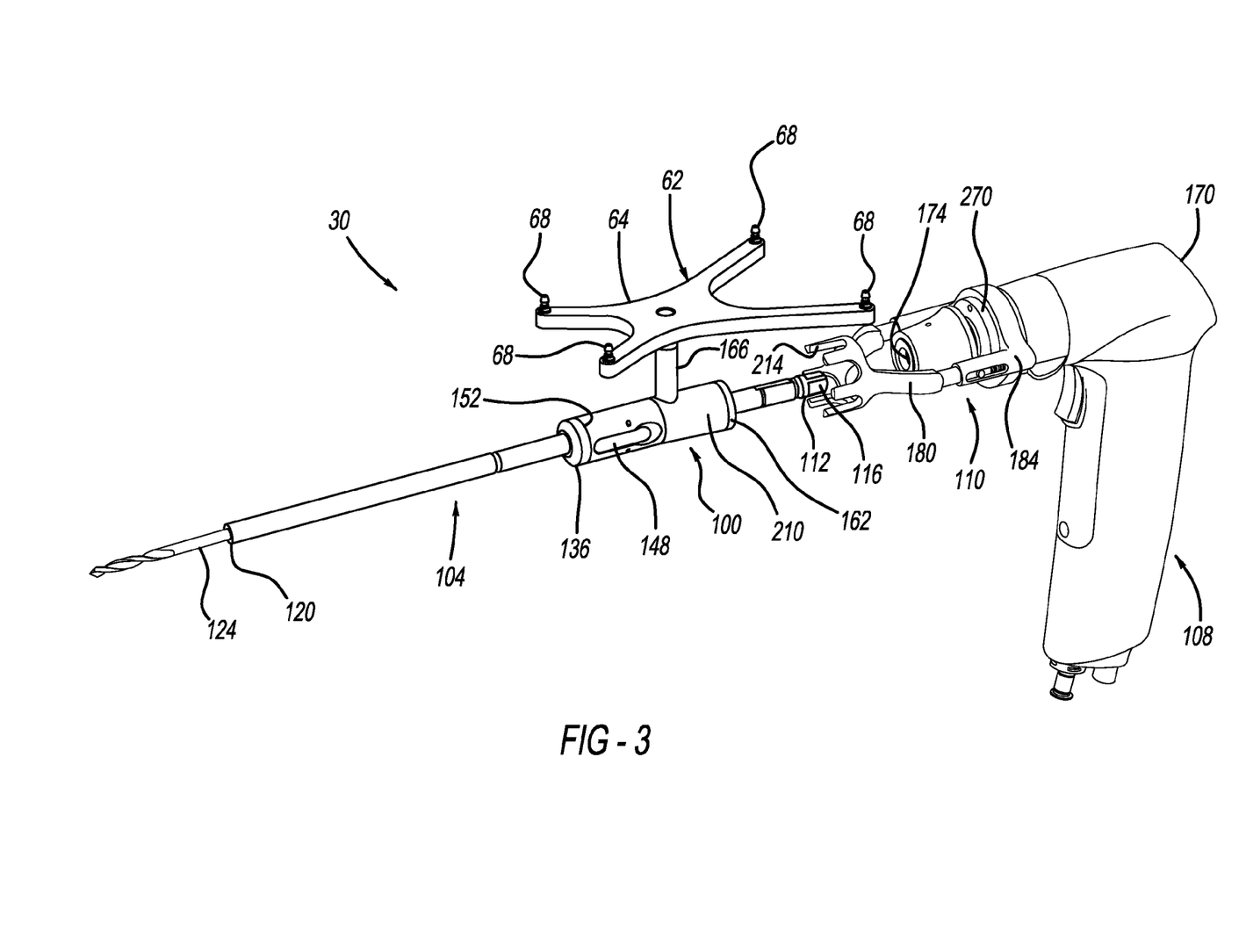
FIG. 3 is a view of the instrument of FIG. 2 shown partially exploded in accordance with the teachings of the present disclosure.
Figure 4:
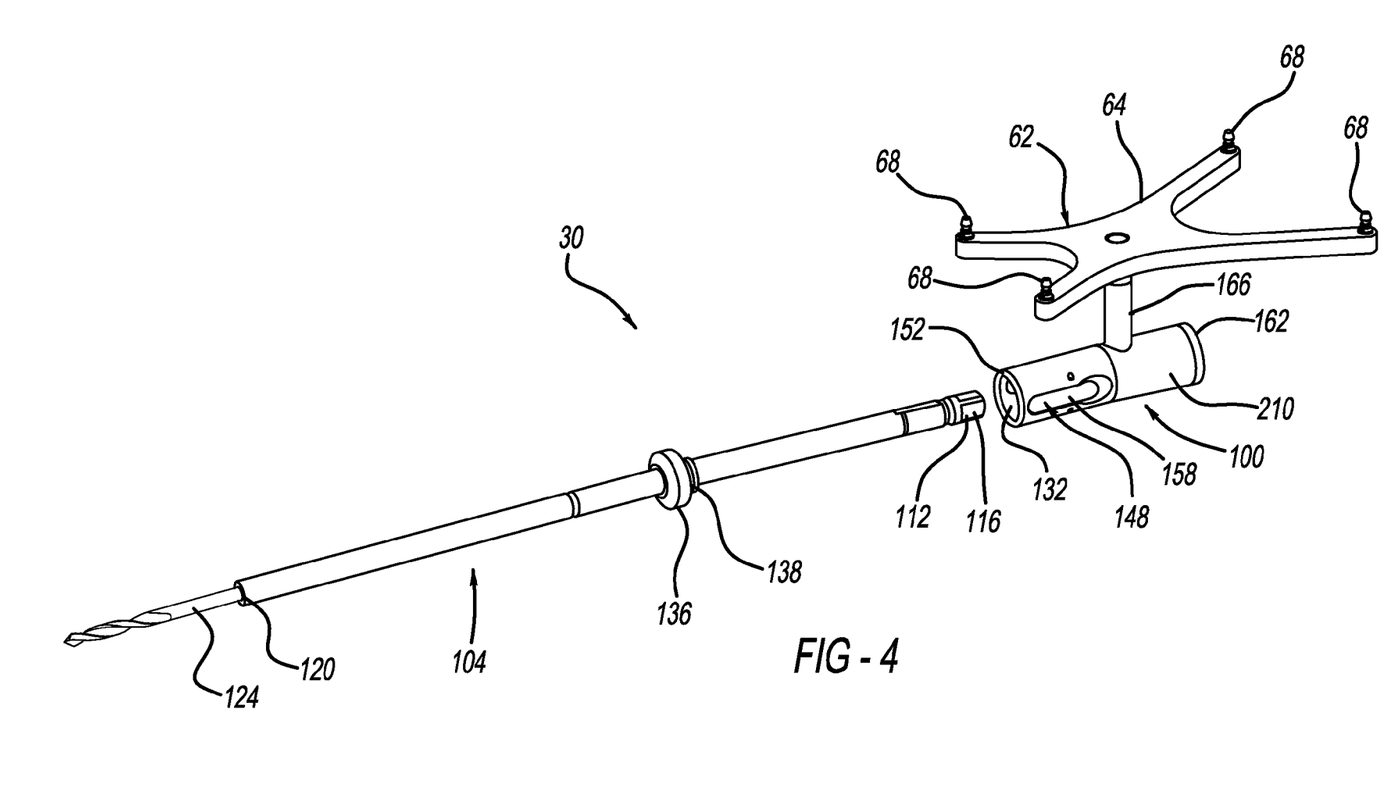
FIG. 4 is a perspective exploded view of an instrument tip and guide member assembly of the instrument of FIG. 2 in accordance with the teachings of the present disclosure.

As briefly discussed above, the stabilizer 110 can be used to selectively and adjustably rotationally fix the tracking array 64 in a desired angular orientation relative to driving device 108. In operation, the second member 184 can be fixed to housing portion 270 in the manner discussed above and the first member 180 can be slidably received over the guide member 100, as generally shown in FIG. 3 with reference to FIG. 2. When instrument tip 104 is coupled to driving device 108 in the manner shown in FIG. 2, the first member 180 can engage the post 166 via one of the locating slots 214 and the second member 184 can engage the projections 278 via depressions 264. In this assembled configuration of instrument 30, a length of the stabilizer 110 can be greater than a distance between post 166 and projections 278 such that when the stabilizer is engaged with post 166 and projections 278, the stabilizer is telescopically compressed against the force of springs 238, as generally shown in FIG. 2.

The length 258 of axially extending slots 234 can be sized to provide for telescopically urging first member 180 into second member 184 and away from post 166 to provide for selectively rotating guide member 100 relative to driving device 108 about instrument tip 104 to a desired angular orientation. With the guide member 100, and thus array 64 in the desired angular orientation, the first member 180 can be allowed to axially translate back toward post 166 under the influence of spring 238 such that one of the locating slots 214 adjacent post 166 engages post 166. This action can selectively fix guide member 100 and associated array 64 in the desired angular orientation without requiring the surgeon to hold guide member 100 during operation of instrument 30 (e.g., rotation of instrument tip 104 by drive device 108). The stabilizer 110 can also efficiently allow the surgeon to easily change the orientation of array 64 relative to driving device 108 during a surgical procedure.

While one or more specific examples have been described and illustrated, it will be understood by those skilled in the art that various changes may be made and equivalence may be substituted for elements thereof without departing from the scope of the present teachings as defined in the claims. Furthermore, the mixing and matching of features, elements and/or functions between various examples may be expressly contemplated herein so that one skilled in the art would appreciate from the present teachings that features, elements and/or functions of one example may be incorporated into another example as appropriate, unless described otherwise above. Moreover, many modifications may be made to adapt a particular situation or material to the present teachings without departing from the essential scope thereof.

What is claimed is:

1. A stabilizer for use with a trackable surgical instrument, comprising:
   a first member having a first annular body portion at a distal end and a first pair of legs extending therefrom and defining a proximal end of the first member, the first annular body portion including a plurality of locating slots adapted to engage a selectively positionable portion of the surgical instrument;
   a second member having a second annular body portion at a proximal end thereof and a second pair of legs extending therefrom and defining a distal end of the second member, the second annular body adapted to engage a drive device of the surgical instrument, the first pair of legs being telescopically coupled with and adjustable relative to the second pair of legs such that the first member is axially adjustable relative to the second member; and
   a retaining member configured to cooperate with at least one leg of the first and second pair of legs to retain the first member adjustably coupled to the second member.

2. The stabilizer of claim 1, further comprising a biasing member configured to bias the first member, when coupled to the second member, away from the second member.

3. The stabilizer of claim 2, wherein each leg of the second pair of legs includes an internal bore, the first pair of legs being telescopically received in the internal bores of the second pair of legs.

4. The stabilizer of claim 3, wherein each leg of the second pair of legs includes at least one axially extending slot captured between terminal ends of each leg of the second pair of legs.

5. The stabilizer of claim 4, wherein the retaining member includes a pair of retaining members, each retaining member being positioned in a respective axially extending slot and in engagement with a respective leg of the first pair of legs.

6. The stabilizer of claim 5, wherein each leg of the first pair of legs includes a transverse bore proximate the proximal end of the first member, the pair of retaining members being received in the respective transverse bores.

7. The stabilizer of claim 3, wherein the biasing member includes a pair of biasing members being positioned in the internal bores and in engagement with the first pair of legs.

8. The stabilizer of claim 1, wherein the second annular body includes at least one locating slot adapted to engage a projection on the drive device to removably couple the second member to the drive device.

9. The stabilizer of claim 1, wherein the second annular body includes an internal groove configured to receive an o-ring, the o-ring adapted to provide a friction coupling between the second member and the drive device.

10. A stabilizer for use with a trackable surgical instrument, comprising:
    a first member having a first body portion at a distal end of the first member and a first pair of legs extending from the first body portion toward a proximal end of the first member, the first body portion having a plurality of slots adapted to engage a selectively positionable portion of the surgical instrument in one of a plurality of rotational orientations; and
    a second member having a second body portion at a proximal end of the second member and a second pair of legs extending from the second body portion toward a distal end of the second member, the second body portion adapted to engage a portion of the surgical instrument, the first pair of legs being coupled with and adjustable relative to the second pair of legs such that the first member is axially adjustable relative to the second member to permit the selectively positionable portion of the surgical instrument to be positioned in one of a plurality of rotational orientations in one of the plurality of slots.

11. The stabilizer of claim 10, further comprising a biasing member configured to bias the first member, when coupled to the second member, away from the second member.

12. The stabilizer of claim 10, wherein at least one of the first pair of legs or the second pair of legs includes a pair of internal bores and wherein the other of the first pair of legs or the second pair of legs being telescopically received in the pair of internal bores.

13. The stabilizer of claim 10, further comprising a retaining member configured to cooperate with at least one leg of the first and second pair of legs to retain the first member adjustably coupled to the second member.

14. The stabilizer of claim 10, wherein the second member having the second body portion includes a second annular body adapted to engage a drive device of the surgical instrument.

15. The stabilizer of claim 14, wherein the second annular body includes at least one locating slot adapted to engage a projection on the drive device to removably couple the second member to the drive device.

16. A stabilizer for use with a trackable surgical instrument having a tracking array, comprising:
- a first member defining a plurality of slots configured to engage a portion of the tracking array to maintain an angular position of the tracking array relative to the surgical instrument; and
- a second member configured to connect to and be in a fixed angular position relative to the surgical instrument, wherein the first member is coupled to the second member and is axially adjustable relative to the second member to disengage the portion of the tracking array to permit rotation of the tracking array relative to the first member, and wherein rotation of the portion of the tracking array relative to the first member changes an angular position of the tracking array relative to the surgical instrument.

17. The stabilizer of claim 16, further comprising a biasing member biasing the first member axially away from the second member.

18. The stabilizer of claim 17, wherein the first member includes a first leg and the second member includes a second leg, wherein the first leg is configured to slide within the second leg and against the biasing member to permit rotation of the tracking array relative to the surgical instrument.

19. The stabilizer of claim 18, wherein the second member includes an annular body configured to be coupled to the surgical instrument.

20. The stabilizer of claim 16, wherein the first member includes a first pair of legs and the second member includes a second pair of legs, the first pair of legs being telescopically coupled with and adjustable relative to the second pair of legs such that the first member is axially adjustable relative to the second member.

* * * * *